United States Patent [19]

Hagiwara et al.

[11] Patent Number: 4,775,585
[45] Date of Patent: Oct. 4, 1988

[54] POLYMER ARTICLE HAVING AN ANTIBACTERIAL PROPERTY CONTAINING ZEOLITE PARTICLES THEREIN AND THE PROCESSES FOR PRODUCING SAME

[75] Inventors: Zenji Hagiwara, Kusatsu; Shigetaka Hoshino, Sohka; Hiroo Ishino, Kitakatsushika; Saburo Nohara, Nishinomiya; Kenichi Tagawa, Osaka; Keio Yamanaka, Toyonaka, all of Japan

[73] Assignee: Kanebo Ltd./Kanto Chemical Co., Tokyo, Japan

[21] Appl. No.: 8,250

[22] Filed: Jan. 29, 1987

Related U.S. Application Data

[63] Continuation-in-part of Ser. No. 572,412, Jan. 20, 1984, abandoned.

[30] Foreign Application Priority Data

Jan. 21, 1983 [JP] Japan .................................. 58-7361

[51] Int. Cl.$^4$ ............................................ B01D 39/08
[52] U.S. Cl. ...................................... 428/323; 264/62; 264/DIG. 25; 428/328; 428/403
[58] Field of Search ............... 428/323, 328, 329, 331, 428/332, 403, 404, 406; 427/2; 210/501; 524/450; 424/132, 140, 145

[56] References Cited

U.S. PATENT DOCUMENTS

| | | | |
|---|---|---|---|
| 1,642,089 | 9/1927 | Schreir | 424/132 X |
| 2,066,710 | 1/1937 | Bado | 424/132 |
| 2,867,605 | 1/1959 | Safford | 524/450 |
| 3,208,984 | 9/1965 | Dekking | 524/450 X |
| 3,862,030 | 1/1975 | Goldberg | 210/501 X |
| 4,071,636 | 1/1978 | Nishino et al. | 210/501 X |
| 4,145,764 | 3/1979 | Suzuki et al. | 427/2 X |
| 4,146,936 | 4/1979 | Aoyagi et al. | 427/2 X |
| 4,222,128 | 9/1980 | Tomonaga et al. | 427/2 X |
| 4,244,824 | 1/1981 | Tange et al. | 210/501 X |
| 4,254,180 | 3/1981 | Kline | 428/323 |
| 4,307,010 | 12/1981 | Sandler et al. | 524/450 |
| 4,326,305 | 4/1982 | Davidas | 427/2 X |
| 4,347,844 | 9/1982 | Ohki et al. | 428/323 X |
| 4,364,985 | 12/1982 | Tokuyama et al. | 428/331 X |
| 4,407,865 | 10/1983 | Nice | 428/403 X |
| 4,463,031 | 7/1984 | Someya | 428/403 X |
| 4,525,410 | 6/1985 | Hagiwara et al. | 424/132 X |

*Primary Examiner*—Nancy A. B. Swisher
*Attorney, Agent, or Firm*—Nixon & Vanderhye P.C.

[57] ABSTRACT

A polymer article containing zeolite particles on which metal ion having a bactericidal property, e.g. Ag, Cu or Zn, is provided by an ion exchange reaction shows an excellent bactericidal effect and durability of the effect, but no deterioration of physical properties of the polymer.

The polymer article is produced by admixing zeolite particles previously provided with the metal ion with a polymer or by moulding a zeolite-containing polymer into an article and then treating the article with a metal ion solution.

15 Claims, 1 Drawing Sheet

POLYMER ARTICLE HAVING AN ANTIBACTERIAL PROPERTY CONTAINING ZEOLITE PARTICLES THEREIN AND THE PROCESSES FOR PRODUCING SAME

CROSS-REFERENCE TO RELATED APPLICATION

This application is a continuation-in-part of earlier application Ser. No. 572,412 filed Jan. 20, 1984, now abandoned.

FIELD OF THE INVENTION

This invention relates to a polymer article having an antibacterial property comprising at least one organic polymer and zeolite particles contained in said polymer and processes of producing same.

BACKGROUND OF THE INVENTION

It has been known for a long time that a silver ion, a copper ion and a zinc ion have an antibacterial property. For example, a silver ion has widely been utilized as a disinfectant or a germicide in the form of a solution of silver nitrate. However, the use of silver nitrate as a form of solution is inconvenient for handling and further there is a fault that such a form can be used only for restricted purposes.

Then, a polymeric substance holding the metallic ions was proposed for a use of various fields to reduce the aforementioned disadvantages. Many methods of incorporating the metal ions into a polymeric substance are known, for example, a method of binding or adding fine wires or powder of the metals themselves to a polymer and a method of incorporating compounds of the metals into a polymer.

However, in such methods as mentioned above, in which the metals themselves are used, there is a disadvantage that the metals show poor compatibility because the specific weights and Young's moduli of the metals are usually very high compared with those of the conventional polymers.

In addition, such metals lead to a heavy weight of products and a high cost as they are necessarily used in a large amount. In a method wherein compounds of the metals are used, a product obtained can be utilized only for restricted purposes because of a heavy influence of the compounds on polymer properties, or else it shows poor durability of an antibacterial performance because the metal ions are merely contained in or attached to a polymer and, accordingly, they easily fall away from a polymer while being used.

For a method having no or less disadvantages as mentioned above, a method was proposed wherein a polymer contains organic functional groups having an ion exchange function or a complex-forming function and thereby these groups retain the metal ions. However, in this method, an adverse effect of these functional groups on physical properties of the polymer can not be disregarded.

Whether the functional groups are chemically introduced into the polymer or compounds having the functional groups are involved in a polymer, a type of polymer and a type and an amount of functional groups capable of being used are limited in order to avoid noticeable change of physical properties of polymers.

SUMMARY OF THE INVENTION

As the result of various investigations for overcoming the foregoing difficulties, the present invention has been attained.

The present invention provides a polymer article having an antibacterial property containing zeolite particles thereon, and also processes of producing said article.

Specifically, the present invention provides a polymer article having antibacterial properties as well as a physical property similar to those of the polymer itself, which contains zeolite particles retaining metal ions which show an antibacterial effect at the ion-exchange sites of the zeolite particles, and processes of producing said article. A great variety of polymers can be used in the present invention.

Thus, according to the present invention, there is provided a polymer article having an antibacterial property characterized in that the polymer article composed of at least one polymer in which are dispersed zeolite particles at least part of which retain at least one metal ion having a bacteriocidal property in the ion-exchange sites of the zeolite particles. Further, the present invention provides two processes for producing the polymer article. One process according to the present invention is characterized by admixing zeolite particles retaining at least one metal ion having a bacteriocidal property with an organic polymer or a mixture of polymers at any stage prior to moulding the organic polymer to form the shaped article.

Another process is characterized in that an organic polymer or a mixture of polymers containing zeolite particles is moulded and then treated with an aqueous solution of at least one water-soluble salt of at least one metal ion having a bacteriocidal property to provide at least part of the zeolite particles with said metal ion.

The articles and processes of preparing them are further characterized in that the zeolite particles have a specific area of at least 150 m$^2$/g, based upon anhydrous zeolite as the standard, and an SiO$_2$/Al$_2$O$_3$ mol ratio of at most 14. In addition, it is required that at least a portion of the zeolite particles retain the metal ions having bacteriocidal properties at ion-exchangable sites of the zeolite in an amount less than the ion-exchange saturation capacity of the zeolite.

BRIEF DESCRIPTION OF THE DRAWINGS

FIGS. 1 and 2 are cross-sectional views of polymer articles according to the present invention. In FIG. 1, A is a polyester component containing zeolite and B is a polyester component containing no zeolite.

DESCRIPTION OF THE PREFERRED EMBODIMENT

The zeolite particles having a bacteriocidal activity to be used in this invention are natural or synthetic zeolite particles retaining one or more metal ions having a bactericidal property at the ion-exchangeable sites thereof. Preferred examples of metal ions having a bactericidal property are ions of Ag, Cu, Zn. These metals can be used solely or as a mixture thereof for the foregoing purposes of this invention.

Zeolite is generally aluminosilicate having a three-dimensionally grown skeleton structure and is generally shown by $xM_{2/n}O.Al_2O_3.ySiO_2.zH_2O$, written with $Al_2O_3$ as a basis, wherein M represents an ion-exchangeable metal ion, which is usually the ion of a monovalent or divalent metal; n corresponds to the valence of the metal; x is a coefficient of the metal oxide; y is a coefficient of silica; and z is the number of water of crystallization. Various kinds of zeolites having different component ratio, fine pore diameter, and specific surface area are known.

However, it is required that the specific surface area of the zeolite particles used in this invention is at least 150 m$^2$/g (anhydrous zeolite as standard) and the $SiO_2/Al_2O_3$ mol ratio in the zeolite composition is at most 14, preferably at most 11.

Since a solution of a water-soluble salt of a metal having a bactericidal activity used in this invention, such as silver, copper and zinc, easily causes an ion exchange with zeolite defined in this invention, the foregoing metal ions can be retained on the solid phase of zeolite solely or as a mixture thereof by utilizing an ion exchange phenomenon. However, the zeolite particles retaining the metal ion or ions must satisfy the conditions that the specific area is at least 150 m$^2$/g and the $SiO_2/Al_2O_3$ mol ratio is at most 14. It has been found that if the zeolite particles do not satisfy the foregoing conditions, a desired product having an effective bactericidal activity cannot be obtained, presumably because the absolute amount of the metal ion or ions fixed to zeolite in the state of exhibiting the effect is insufficient. In other words, the effect is considered to depend on the physicochemical properties such as the amount of the exchange groups of zeolite, the exchange rate, the accessibility, etc.

Therefore, a zeolite having a larger $SiO_2/Al_2O_3$ mol ratio which is known as a molecular sieve is utterly unsuitable in the present invention.

Also, it has been found that zeolite having a $SiO_2/Al_2O_3$ mol ratio of at most 14 can uniformly retain the metal ion having a bactericidal activity, whereby a sufficient bactericidal activity can be obtained. In addition, the acid resistance and alkali resistance of zeolite having a larger $SiO_2/Al_2O_3$ mol ratio over 14 become better with the increasing content of $SiO_2$ but, on the other hand, it takes a long period of time to prepare such a zeolite and hence the use of the zeolite having such a high silica content is not profitable from economic aspect. The natural or synthetic zeolite having a $SiO_2/Al_2O_3$ mol ratio of at most 14 shows sufficient acid resistance and alkali resistance for an ordinary application of the article as well as is inexpensive from economical aspect and, therefore, can be advantageously used. From these viewpoints, it is required that the $SiO_2/Al_2O_3$ mol ratio of the zeolite particles be at most 14.

As the zeolite material having a $SiO_2/Al_2O_3$ mol ratio of at most 14 used in this invention, any natural or synthetic zeolites can be used. Examples of natural zeolite to be used in this invention are analcime ($SiO_2/Al_2O_3 = 3.6$ to 5.6), chabazite ($SiO_2/Al_2O_3 = 3.2$ to 6.0 and 6.4 to 7.6), clinoptilolite ($SiO_2/Al_2O_3 = 8.5$ to 10.5), erionite ($SiO_2/Al_2O_3 = 5.8$ to 7.4), faujasite ($SiO_2/Al_2O_3 = 4.2$ to 4.6), mordenite ($SiO_2/Al_2O_3 = 8.34$ to 10.0), phillipsite ($SiO_2/Al_2O_3 = 2.6$ to 4.4). These typical natural zeolites can be preferably used in this invention. On the other hand, typical examples of synthetic zeolites to be used in this invention are A-type zeolite ($SiO_2/Al_2O_3 = 1.4$ to 2.4), X-type zeolite ($SiO_2/Al_2O_3 = 2$ to 3), Y-type zeolite ($SiO_2/Al_2O_3 = 3$ to 6), mordenite ($SiO_2/Al_2O_3 = 9$ to 10). Particularly preferred examples of the zeolites used in this invention are synthetic A-type zeolite, X-type zeolite, Y-type zeolite and synthetic or natural mordenite.

The suitable shape of zeolite used in this invention may preferably be fine particulate.

A particle size of the zeolite can suitably be selected depending on application fields. When a moulded article according to the present invention has a relatively large thickness, like various types of containers, pipes, granules or coarse fibers, the particle size may be in the range of a few microns to tens microns or even above several hundred microns. When fibers or films are moulded as an article according to the present invention, preference is given to a smaller size of particle. For instance, the particle size of 5 microns or less, especially 2 microns or less is preferred for fibers to be used in clothes.

According to the present invention, the zeolite particles should retain the bacteriocidal metal ion in an amount less than an ion-exchange saturation capacity of the zeolite. It has now been found that if the amount of the metal ion is as large as the ion exchange capacity of the zeolite or even greater, the bacteriocidal effect of the polymer article is very poor. It is believed that when the metal ion in amounts such as to saturate the ion-exchange capacity of the zeolite are given to the zeolite, a portion of the metal ion deposits on the surface of zeolite in a form other than an ion, such as silver oxide (in the case of silver ions), or basic salts of copper or zinc. These oxides have been found to be very detrimental to the bacteriocidal effect of the zeolite-metal ion. The adverse effect of a saturating amount of the bacteriocidal metal is shown in Example 6 to follow. Preferably, the zeolite particles retain the metal ion in an amount of less than 92%, more preferably 85%, particularly 70%, of the ion exchange capacity of the zeolite. Even when the amount of the metal ion is well below the ion exchange capacity of the zeolite, some deposition of the metal compound may occur under certain conditions. In order to avoid such deposition, the metal ion may be supplied from a dilute metal ion solution, if necessary, through repeated procedures, as will be explained below.

Organic polymers to be used in the present invention include synthetic and semi-synthetic organic polymers and are not limited to any specific ones. Examples of suitable organic polymers are thermoplastic synthetic polymers, such as polyethylene, polypropylene, polystyrene, polyvinyl chloride, polyvinylidene chloride, polyamides, polyesters, polyvinyl alcohol, polycarbonates, polyacetals, ABS resins, acrylic resins, fluorine-contained resins, polyurethane elastomers, polyester elastomers; thermosetting synthetic polymers such as phenolic resins, urea resins and urethane resins; regenerated or semi-synthetic polymers such as rayon, cuprammonium rayon, acetate rayon, triacetate rayon. When a high degree of bacteriocidal effect is desired, the moulded article preferably has a large surface area.

This can be attained, for instance, by moulding materials into a fibrous shape. From this aspect, preferably organic polymers are fiber-forming ones, for instance, synthetic polymers such as Nylon 6, Nylon 66, polyvinyl alcohol, polyvinyl chloride, polyvinylidene chloride, polyethylene terephthalate, polybutylene terephthalate, polyacrylonitrile, polyethylene, polypropylene and copolymers thereof; regenerated or semi-synthetic polymers such as rayon, cuprammonium rayon, acetate rayon and triacetate rayon.

The polymer article containing zeolite particles according to the present invention comprises the aforementioned zeolite particles and at least one of the aforementioned organic polymers; at least part of said zeolite particles retaining therein at least one metal ion having a bacteriocidal property.

Zeolite particles account for 0.01 to 10% by weight of the whole article, based on anhydrous zeolite. If zeolite is used in an amount of less than 0.01% by weight, only a poor and insufficient bacteriocidal activity is obtained. On the other hand, if zeolite is used in an amount of more than 10% by weight, an incremental activity is hardly obtained and, in addition, a noticeable change in the physical properties of a resulting polymer article is observed whereby the application of the polymer article is limited. Thus, the preferable content of zeolite particles ranges from 0.05 to 10% by weight, especially when the polymer article according to the present invention is fibrous.

The metal ions should be retained on the zeolite particles through an ion-exchange reaction. Metal ions which are merely adsorbed or attached without using an ion-exchange reaction show a poor bacteriocidal effect and an insufficient durability.

The present inventors have found two alternative processes which enable strong retention of the ions on the zeolite particles.

In the first process, metal-zeolite having a bacteriocidal function is added to an organic polymer or a mixture of polymers mixed together.

In the second process, zeolite is added to an organic polymer or a mixture of polymers, mixed together and, then moulded. Thereafter the polymer article thus obtained is rendered to an ion-exchange treatment to let the zeolite in the polymer article retain the metal ions having a bacteriocidal property.

At first, the first process will be described hereinafter.

In this process, the metal-zeolite having a bacteriocidal activity can be prepared by utilizing the ion exchange reaction as described above. For example, in the case of preparing the Ag-zeolite of this invention using various kinds of zeolites as defined in this invention, an aqueous solution of a water-soluble silver salt such as silver nitrate is usually used at the conversion to the Ag-zeolite and in this case it must be noted that the concentration of the solution does not become too high. For example, if the silver ion concentration is too high, e.g. $AgNO_3$ of 1 to 2 molarity (molarity is hereinafter referred to as M), in the case of converting an A-type zeolite or an X-type zeolite (i. e., sodium-type zeolite) into an Ag-zeolite by utilizing an ion-exchange reaction, the silver ion in the solution forms silver oxide onto the solid phase of the zeolite as precipitates simultaneously when the silver ion is replaced with the sodium ion of the solid phase of the zeolite. The precipitation of the silver oxide on the zeolite reduces the porosity of the zeolite, whereby the specific surface area of the zeolite is greatly reduced. Also, even when the reduction of the specific surface area of the zeolite is not so serious, the bactericidal activity of the Ag-zeolite is reduced by the presence of the silver oxide itself. For preventing the deposition of such excessive silver onto the solid phase of zeolite, it is necessary to maintain the concentration of the silver solution at a diluted state, e. g., lower than 0.3M $AgNO_3$, preferably lower than 0.1M $AgNO_3$. It has been found that in the case of using an aqueous $AgNO_3$ solution of such a concentration, the specific surface area of the Ag-zeolite thus obtained is almost same as that of the original zeolite and the bactericidal function can be utilized at the optimum condition.

In the case of converting the zeolite defined in this invention into a Cu-zeolite, the same phenomenon as mentioned above for an Ag-zeolite will take place depending on a concentration of a solution of a copper salt used for the ion-exchange reaction. For example, when an aqueous solution of 1M $CuSO_4$ is used in the case of converting an A-type or an X-type zeolite (sodium-type zeolite) into a Cu-zeolite by an ion-exchange reaction, $Cu^{2+}$ in the solution is replaced with $Na^+$ of the solid phase of the zeolite but, at the same time, basic precipitates such as $Cu_3(SO_4)(OH)_4$ deposit onto the solid phase of the zeolite, whereby the porosity of the zeolite is reduced and thus the specific surface area thereof is also greatly reduced. For preventing the deposition of the copper onto the solid phase of zeolite, it is preferred to maintain the concentration of an aqueous solution of a water-soluble copper salt used in this invention at a diluted state, for example, lower than 0.05M. It has also been found that in the case of using an aqueous $CuSO_4$ solution of such a concentration. the specific surface area of the Cu-zeolite obtained is almost same as that of the original zeolite and the bactericidal function can be utilized at the optimum condition.

As stated above, at the conversion into an Ag-zeolite or Cu-zeolite, there is a deposition of a solid material onto the solid phase of the zeolite depending on the concentration of a salt used for the ion-exchange reaction. However, at the conversion into a Zn-zeolite, there occurs none of such a phenomenon when the concentration of a solution of a salt used is about 2 to 3M. Usually, the Zn-zeolite to be used in this invention can be easily obtained by using a solution of a zinc salt having the foregoing concentration of 2 to 3M.

When the ion-exchange reaction for the conversion into an Ag-zeolite, a Cu-zeolite or a Zn-zeolite is performed in a batch method, the zeolite may be immersed in the metal salt solution having the foregoing concentration. In order to increase the content of a metal in the zeolite, the batch treatment may be repeated. On the other hand, in the case of treating the foregoing zeolite in a column method using a metal salt solution having the aforesaid concentration, the desired metal-zeolite is easily obtained by packing the zeolite in an adsorption column and passing the solution of the metal salt through the column.

The amount of the metal incorporated in the aforesaid metal-zeolite may be less than 30% by weight, preferably 0.001 to 5% by weight in the case of silver, based on anhydrous zeolite plus metal. On the other hand, in the case of zinc or copper, the amount of zinc or copper incorporated in the metal-zeolite may be less than 35% by weight, preferably 0.01 to 15% by weight, based on anhydrous zeolite plus metal. It is possible to use two or three of silver, copper and zinc ions together. In this case, the total amount of the metal ions may be less than 35% by weight, based on anhydrous-zeolite plus metal. The amount ranges preferably from about 0.001 to about 15% by weight depending on the composition of metals used.

Further, metal ions other than silver, copper and zinc ions, such as sodium, potassium, calcium and so on may remain or co-exist in the metal-zeolite since such ions do not prevent the bactericidal effect.

In the next step of the first process, the metal-zeolite thus obtained is added to the organic polymer in such an amount that the aforementioned content of the zeolite may be attained to obtain a composition according to the present invention. Both the ratio of the metals having a bactericidal property to the metal-zeolite, referred to as A (wt. %), and the ratio of the metal-zeolite to the whole composition, referred to as B (wt. %), have a relation with a bactericidal performance. A bigger A permits a smaller B and, on the other hand, a smaller A requires a larger B.

To obtain an efficient performance of the bactericidal function, it is preferred to adjust the product A by B above 0.01 for the silver-zeolite, or above 0.1 for the copper-or zinc-zeolite.

A time and a means of adding and mixing are not particularly restricted. Various manners may be utilized, such as a way of adding the metal-zeolite into a raw monomer or an intermediate product and carrying out polymerization, a way of adding the metal-zeolite to a polymer after polymerization, a way of adding the metal-zeolite to polymer pellets, followed by moulding, and a way of adding the metal-zeolite into a moulding dope, for instance, a spinning solution. For short, all these manners are herein referred to as "adding zeolite to a polymer and mixing them." The best way will be chosen depending on the nature of a polymer used and the feature of a processing in each case. In general, it is preferred to add the metal-zeolite to a polymer immediately before moulding. However, in some cases, it may be preferable to add the metal-zeolite into a monomer so as to attain a good dispersion of zeolite particles. The metal-zeolite may, if desired, be dried before its addition to a polymer. A drying condition can properly be chosen in the range of a temperature from 100° to 500° C. under an atmospheric or a reduced pressure, preferably 100° to 500° C. under a reduced pressure.

Next, the second alternative process according to the present invention will be described hereinafter.

Basically, the second process has many things in common with the first process, though a time for the ion-exchange treatment in the second process differs from that in the first process. In the second process, the zeolite as defined above is first added to a polymer and mixed without an ion-exchange treatment. The possible range of a content of the zeolite is the same as that in the first process. Zeolite may be added at any time from a stage of preparation of raw materials for polymerization to a stage of moulding, as in the first process. If drying of zeolite is needed, this can be done in a similar manner as described above in the first process.

The resulting polymer containing zeolite is moulded into an article and, then, subjected to an ion-exchange treatment. There is no special limitation for a type or shape of the article. The article can be an intermediate produce such as pellet or a final product. An article having a large specific surface area is preferred to attain a high efficiency of the ion-exchange. Thus, an article having a small diameter or thickness is preferred, such as granules, films and fibers. The manner of ion-exchange treatment is basically similar to that in the first process mentioned above. That is, a polymer article containing zeolite is treated with a solution of a water-soluble salt of metal having a bactericidal property. In this process, the concentration of a metal salt is preferably less than 0.3M, especially less than 0.1M, for Ag NO$_3$, and less than 0.05M for CuSO$_4$. When the concentration of a silver or copper salt is too high, silver oxide or basic precipitates of copper appear to cause a problem of reduction of the bactericidal effect. In case of using a zinc salt, since there occurs no such a phenomenon, a concentration around 2~3M may be used for the treatment. The treatment may be carried out either batchwise or continuously. In order to increase the amount of metal ions retained in the article, the batch treatment may be repeated or the period of time of continuous treatment may be prolonged.

The second alternative process has been deprived from the finding that the zeolite contained in a polymer articles still keeps its ability of ion-exchange and it is possible to let said zeolite retain the metal ions having bactericidal property by a proper ion-exchange treatment. It depends on the nature of a polymer in each case how much zeolite in a polymer article be ion-exchanged. In case of a relatively highly hydrophilic polymer, since the metal ions penetrate into the deeper part of an article as water penetrates, even the zeolite present in the deeper part of the article in ion-exchanged.

Further, even in case of a hydrophobic polymer, it has been found that the zeolite present around the surface area is ion-exchanged to a considerable extent. Since the bactericidal performance of a polymer article containing zeolite particles seems to be attributed to the metal ions present around the surface are of the article, the fact that only the zeolite present near the surface area retains the metal ions having a bactericidal property does not cause any problem and this is even preferable in terms of effective use of the metal ions having a bactericidal property. In any case, the ratio of the metal ions having bactericidal property to the total weight of zeolite (based on anhydrous zeolite) plus metal may be less than 30% by weight, preferably 0.001 to 5% by weight in case of using silver. In case of using copper or zinc, this may be less than 35% by weight, preferably 0.01 to 15% by weight. In the case that silver, copper and zinc ions are used together, the total amount of the metal ions is preferably in the range of from 0.001 to 15% by weight. Further, metal ions other than the above three may remain or co-exist in the article.

As mentioned regarding the first process, the ratio of the metals retained in the zeolite by the ion-exchange to the metal-zeolite, referred to as A (wt. %), and the ratio of the zeolite contained in a polymer to the whole article, referred to as B (wt. %) have a relation with a bactericidal performance. When B is bigger, A may be smaller. On the other hand, when B is smaller, a A must be bigger. It is preferred to adjust the product A by B above 0.01 for silver-zeolite, or above 0.1 for copper- or zinc-zeolite.

The polymer article containing zeolite particles according to the present invention may contain components other than metal-zeolite, such as polymerization catalysts, stabilizers, delustering agents, optical whitening agents, organic or inorganic pigments, inorganic fillers, various plasticisers and so on. The article may contain liquid or organic solvents as other components. When the polymer article containing zeolite particles according to the present invention is a moulded article, its shape and dimension are not specially limited. A manner of distribution of metal-zeolite in the moulded article may suitably be thought out.

Since the bactericidal performance of the polymer article according to the present invention relies on the amount of metal ions present around the surface area of the article, it is an efficient manner to localize the metal-zeolite (in the first process) or the zeolite (in the second process) around the outer surface area of the moulded article. For instance, it is considered that an article has a layered structure and its outer layer contains the metal-zeolite or the zeolite according to the present invention. In case of a fiber article, fibers may be given a sheath-core structure by using a known technique of preparing a conjugated yarn. The sheath contains the metal-zeolite or the zeolite according to the present invention.

The bonding strength between the zeolite defined in this invention and an antibacterial metal ion such as zinc, silver and copper ions is very high unlike the case of making the metal ion retain onto an adsorptive material such as activated carbon, alumina, etc., simply by a physical adsorption. Therefore, the strong bactericidal performance of the polymer article containing such a metal-zeolite and an excellent durability of the bactericidal effect are the specific features of this invention.

The zeolite defined in this invention has an advantage that the reactivity thereof with a metal having a bactericidal activity, such as Ag, Cu, and Zn is high. For example, the ion-exchangeable metal ion ($Na^+$) in an A-type zeolite, an X-type zeolite, a Y-type zeolite, or chabazite easily causes an ion-exchange reaction with $Ag^+$, $Cu^{2+}$, or $Zn^{2+}$ to retain bactericidal metal ion in the zeolite with a high retaining power. Also, the zeolite defined in this invention has an advantage that the selectivity for the adsorption of $Ag^+$, $Cu^{2+}$, or $Zn^{2+}$ is high. Such a fact means that even when the polymer article of this invention is used in a liquid or water containing various metal ions for the purpose of pasteurization, $Ag^+$, $Cu^{2+}$, or $Zn^{2+}$ is stably retained in the zeolite for a long period of time as well as the bactericidal activity of the article can be maintained for a long period of time.

In addition, the zeolite defined in this invention also has such an advantage that its ion-exchange capacity is large and, therefore, a large amount of $Ag^+$, $Cu^{2+}$, or $Zn^{2+}$ having a bactericidal activity can be retained in the zeolite. Furthermore, the zeolite defined in this invention has an advantage that the amount of $Ag^+$, $Cu^{2+}$, or $Zn^{2+}$ to be contained in the zeolite particles can be easily controlled in an ion exchange treatment in accordance with the purpose of using the article of this invention.

The zeolite defined in this invention scarcely deteriorates the physical properties of the polymer article obtained and, therefore, a great variety of polymers can be used.

Furthermore, since the polymer article containing the zeolite particles according to the present invention comprising a large proportion of a polymer, it is possible to mould the article having various shapes and dimensions such as granules, films, fibers, various types of containers, pipes and any other moulded articles. They may be used in extremely various fields. The polymer containing the zeolite particles according to the present invention may be fluidized by dissolving or dispersing them into a liquid and such a fluid material may be utilized for an antibacterial paint or a coating material, or a jointing agent to form a film or a block.

In addition, since the polymer article containing the zeolite according to the present invention has the bacteriocidal property and the intrinsic properties of zeolite itself as well, these properties may be utilized at the same time. It is possible to synergistically exploit one of the intrinsic properties of zeolite, for instance, a moisture adsorption and desorption function, and the bacteriocidal property at the same time.

Furthermore, it is also possible to include other functional materials in the polymer article and thereby obtain a combination of the above effects and the effects of these functional materials. Functional materials to be used include activated carbon for deodorization and adsorption, and silicagel for moisture adsorption.

The moulded polymer article containing zeolite particles according to the present invention can be used in a mixed or combined form with the same or different kind of moulded articles which are per se out of the scope of the present invention. For instance, the fibers or the yarns according to the present invention can be mix spun, mix woven, cross woven or union knitted with fibers or yarns having no metal-zeolite to give an antibacterial fiber article with various feelings and functions.

The present invention has such a remarkable advantage that the antibacterial metal ion distributes in the polymer article or around the surface area thereof in a form of being carried on the zeolite, that is to say, the metal ion distributes more evenly in the present invention than in the case of using the metal ion itself without zeolite and, therefore, this fact makes it possible to fully exploit the antibacterial property of the metal ion. In addition, the metal ion is, as mentioned above, retained stably in the zeolite for a long period of time, whereby the polymer article shows an excellent durability of the bacteriocidal effect.

The invention will be further explained hereinafter by the following examples, but these should not be deemed to limit the present invention.

The evaluation of a bactericidal effect in Examples were performed by the following test methods:

(1) Test Method for evaluation of a bactericidal activity:

A bactericidal activity test by a disc method was used. A polymer article containing zeolite particles was cut into a disc of 20 mm in diameter to provide a test disc. In a test, *Escherichia coli, Pseudomonas aeruginosa, Staphylococcus aureus* as bacteria, and *Candida albicans* as Eumycetes were used. A Mueller Hinton culture medium was used for bacteria and a Sabouraud medium was used for Eumycetes. Test bacteria or fungi were floated on a physiological saline solution at $10^8$/ml and then was dispersed in the culture medium by means of a Conradi rod of 0.1 ml. Then, the test disc was placed on the medium. The bactericidal activity was evaluated by observing the presence of an inhibition zone formation after cultivating for 18 hours at 37° C. in the case of bacteria and by observing the presence of an inhibition zone formation after cultivating for one week at 30° C. in the case of Eumycetes.

(2) Method of measuring an extinction rate of Eumycetes:

A moulded polymer article containing zeolite was immersed in a suspension of the spores ($10^4$ spores/ml) of *Asperigillus flavus* for 24 hours at 30° C. Then, the suspension was sampled, diluted, and the diluted sample was dispersed in a Sabouraud agar medium and then maintained for 24 hours at 30° C. Thereafter, the number of living spores was measured and the extinction rate was calculated.

Example For Reference 1

Properties of unconverted, natural or synthetic zeolite used in Examples are shown in Table 1. Each of raw zeolite was crushed and classified to obtain particles having a desired size. As shown in Table 1, A-type zeolite, X-type zeolite, Y-type zeolite, natural modenite 1, natural mordenite 2 and natural chabazite are hereinafter abbreviated as $Z_1$, $Z_2$, $Z_3$, $Z_4$, $Z_5$ and $Z_6$, respectively. Table 1 also shows the particle sizes, the water contents and the specific surface areas of these zeolites.

To 250 g of the fine, dry powder of each zeolite was added 500 ml of an aqueous 1/10M silver nitrate solution and the mixture thus obtained was stirred for 3 hours at room temperature to perform the ion exchange. After filtering the silver-zeolite obtained by such an ion-exchange, the silver-zeolite was washed with water to remove excessive silver ion. Then, the silver-zeolite thus washed was dried at 100° to 105° C. and then crushed to provide fine powder of the silver-zeolite. The silver contents and the specific surface areas of the dry silver-zeolites thus obtained are shown in Table 2.

of the copper-zeolites converted by the foregoing method are shown in Table 2. Regarding the converted copper-zeolite, the copper-A-type zeolite is abbreviated as $Z_{13}$; the copper-Y-type zeolite as $Z_{14}$; the copper-natural mordenite 1 as $Z_{15}$ and the copper-natural chabazite as $Z_{16}$.

Example For Reference 3

To 250 g of the dry powder of the A-type zeolite ($Z_1$) described in Table 1 was added 1000 ml of an aqueous 2M zinc chloride solution and the resultant mixture was stirred for 3 hours and 20 minutes at 60° C. The zinc-zeolite thus obtained by such an ion exchange was separated by centrifugation. Thereafter, the foregoing batch process was repeated. In this example, the treatment by such a batch process was repeated four times. The zinc-zeolite finally obtained was washed with water to re-

TABLE 1

| Abbreviation | Converted zeolite | Composition and origin of zeolite | Particle size | Water content (wt. %) after drying at 100° C. | Specific surface area (m²/g) |
|---|---|---|---|---|---|
| $Z_1$ | A-type zeolite | $0.94Na_2O.Al_2O_3 1.92SiO_2.xH_2O$ | 1.1μ, av. | 16.0 | 664 |
| $Z_2$ | X-type zeolite | $0.99Na_2O.Al_2O_3.2.55SiO_2.xH_2O$ | 1.6μ, av. | 19.8 | 838 |
| $Z_3$ | Y-type zeolite | $1.14Na_2O.Al_2O_3.4.90SiO_2.xH_2O$ | 0.6μ, av. | 12.7 | 908 |
| $Z_4$ | Natural mordenite 1 | Made by Shin Tohoku Kagaku Kogyo Ltd.; $SiO_2/Al_2O_3 = 9.8$ | 2.0μ, av. | 6.7 | 341 |
| $Z_5$ | Natural mordenite 2 | 2020A, trade name, made by Anaconda Minerals Company | passed through a 200 mesh screen | 6.8 | 186 |
| $Z_6$ | Natural chabazite | 5050L, trade name, made by Anaconda Minerals Company | passed through a 200 mesh screen | 10.9 | 498 |

Regarding the converted silver-zeolites, the silver-A-type zeolite is abbreviated as $Z_7$; the silver-X-type zeolite as $Z_8$; the silver-Y-type zeolite as $Z_9$; the silver-natural mordenite 1 as $Z_{10}$; the silver-natural mordenite 2 as $Z_{11}$ and the silver-natural chabazite as $Z_{12}$.

Example For Reference 2

Out of the six types of the natural or synthetic zeolites shown in Table 1, four types were chosen as samples. To 250 g of each dry powder sample was added 1000 ml of an aqueous 1/20M copper sulfate solution and the resultant mixture was stirred for 5 hours at room temperature to perform an ion-exchange reaction. Then, the copper-zeolite thus obtained by such an ion-exchange was filtered by suction and washed with water until the sulfate ion disappeared. Thereafter, the washed copper-zeolite was dried at 100°–105° C. and pulverized to provide fine powder of converted copper-zeolite. The copper content and the specific surface area of each move excessive zinc ion. Then, the Zn-zeolite was dried at about 100° C. and pulverized to provide fine powder of the zinc-A type zeolite.

Also, to 250 g of each of two kinds of dry powder, i.e., the X-type-Zeolite ($Z_2$) and the natural mordenite 2 ($Z_5$) was added 1000 ml of an aqueous 1/20M zinc sulfate solution and the resultant mixture was stirred for 5 hours at room temperature to perform an ion exchange. The zinc-zeolite was filtered by suction and washed with water until the sulfate ion disappeared. Then, the washed zinc-zeolite was dried at 100–105° C. and then pulverized to provide fine powder of zinc-zeolite.

The zinc contents and the specific surface areas of 3 kinds of the zinc-zeolites obtained in the foregoing methods are shown in Table 2.

Regarding the converted zinc-zeolite, the zinc-A-type-zeolite is abbreviated as $Z_{17}$; the zinc-X-type-zeolite as $Z_{18}$ and the zinc-natural mordenite as $Z_{19}$.

TABLE 2

| Abbreviation | Converted zeolite | Particle size | Water content (wt. %) after drying at 100° C. | Metal Species | Metal Content (wt. %), based on anhydrous zeolite | Specific surface area (m²/g) | Metal amount ion exchange capacity (%) |
|---|---|---|---|---|---|---|---|
| $Z_7$ | Silver-A-type zeolite | 1.1μ, av. | 12.1 | Ag | 2.39 | 629 | 5.1 |
| $Z_8$ | Silver-X-type zeolite | 1.6μ, av. | 14.0 | Ag | 2.44 | 831 | 5.5 |
| $Z_9$ | Silver-Y-type zeolite | 0.6μ, av. | 12.5 | Ag | 2.03 | 875 | 5.4 |
| $Z_{10}$ | Silver-natural mordenite 1 | 2.0μ, av. | 5.8 | Ag | 1.20 | 329 | 5.8 |
| $Z_{11}$ | Silver-natural mordenite 2 | passed through a 200 mesh screen | 6.2 | Ag | 0.25 | 174 | 3.4 |
| $Z_{12}$ | Silver-natural chabazite | passed through a 200 mesh screen | 11.1 | Ag | 0.19 | 474 | 1.0 |
| $Z_{13}$ | Copper-A-type zeolite | 1.1μ, av. | 13.2 | Cu | 0.73 | 649 | 3.6 |
| $Z_{14}$ | Copper-Y-type zeolite | 1.6μ, av. | 11.6 | Cu | 1.37 | 903 | 9.3 |
| $Z_{15}$ | Copper-natural mordenite 1 | 2.0μ, av. | 6.5 | Cu | 0.31 | 337 | 4.4 |
| $Z_{16}$ | Copper-natural chabazite | passed through | 11.4 | Cu | 0.11 | 506 | 1.4 |

TABLE 2-continued

| Abbreviation | Converted zeolite | Particle size | Water content (wt. %) after drying at 100° C. | Metal Species | Metal Content (wt. %), based on anhydrous zeolite | Specific surface area ($m^2/g$) | Metal amount ion exchange capacity (%) |
|---|---|---|---|---|---|---|---|
| $Z_{17}$ | Zinc-A-type zeolite | 1.1μ, av. a 200 mesh screen | 12.0 | Zn | 19.9 | 460 | 90.1 |
| $Z_{18}$ | Zinc-X-type zeolite | 1.6μ, av. | 13.4 | Zn | 0.82 | 826 | 4.3 |
| $Z_{19}$ | Zinc-natural mordenite 2 | passed through a 200 mesh screen | 6.4 | Zn | 0.85 | 171 | 11.6 |

EXAMPLE 1

The silver-A-type zeolite ($Z_7$), the silver-X-type zeolite ($Z_8$), the silver-Y-type zeolite ($Z_9$) or the silver-natural mordenite described in Table 2 were dried at 200° C. at a reduced pressure for 7 hours. Then, each of the powder thus dried was admixed with dry chips of Nylon 6 (a relative viscosity ηrel=2,3 in 95% sulfuric acid) in an amount to provide a concentration of 2% by weight of the metal-zeolite. The mixture thus obtained was melted, spun and drawn, according to a conventional technique to four types of drawn yarns having a fineness of 120 deniers / 4 filaments. These yarns were circular-knitted and scoured and then subjected to evaluation of a bactericidal effect. In addition, in order to evaluate a durability of an antibacterial effect, each knitted fabric was washed 50 times according to JIS (Japanese Industrial Standard) L-0217 (Method 105) and, then, subjected to evaluation of an antibacterial effect. In this test, *Candida albicans* was used as a test fungus.

The results of the tests of the antibacterial effect, the extinction rate of Eumycetes and the durability of the antibacterial effect are shown in Tables 3, 4 and 5, respectively.

TABLE 3

Evaluation of antibacterial effect

| Bacteria or fungus | Metal-zeolite added to Nylon 6 | | | |
|---|---|---|---|---|
| | $Z_7$ | $Z_8$ | $Z_9$ | $Z_{10}$ |
| *Escherichia coli* | + | + | + | + |
| *Pseudomonus aeruginosa* | + | + | + | + |
| *Staphylococcus aureus* | + | − | − | + |
| *Candida albicans* | + | + | + | + |

TABLE 4

Extinction rate of Eumycetes

| Eumycetes | Metal-zeolite added to Nylon 6 | | | |
|---|---|---|---|---|
| | $Z_7$ | $Z_8$ | $Z_9$ | $Z_{10}$ |
| *Aspergillus flavus* | 100% | 95% | 95% | 100% |

TABLE 5

Evaluation of durability of antibacterial effect

| Fungus | Metal-zeolite added to Nylon 6 | | | |
|---|---|---|---|---|
| | $Z_7$ | $Z_8$ | $Z_9$ | $Z_{10}$ |
| *Candida albicans* | + | + | + | + |

As can be seen from Table 3, the polymer article containing zeolite particles according to the present invention had an antibacterial effect on more than three species of bacteria or fungus shown in Table 3. The extinction rate of *Aspergillus flavus* exceeded 90% as shown in Table 4. Furthermore, it was confirmed that the anti-bacterial effect lasted after repeating the washing 50 times, as can be seen from Table 5.

Comparison Example 1

Each of fine, dry powder of unconverted $Z_1$, $Z_2$, $Z_3$ and $Z_4$ as described in Table 1 was admixed with Nylon 6, spun and drawn to obtain four types of drawn yarns having a fineness of 120 deniers/4 filaments, according to the same procedure as in Example 1. Then, the evaluation of an antibacterial effect and the test of an extinction rate of Eumycetes were conducted on knitted fabrics made of the above yarns using the same manner and the same bacteria and fungus as in Example 1. In every case, no inhibition zone was formed and the extinction rate was zero, thus no effect was observed.

EXAMPLE 2

Figure 1:
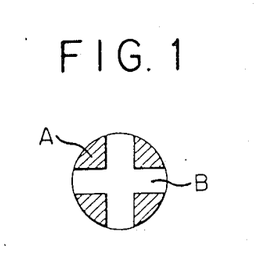

The copper-A-type zeolite ($Z_{13}$), the copper-Y-type zeolite ($Z_{14}$) and the copper-natural mordenite ($Z_{15}$) as described in Table 2 were dried at 200° C. at a reduced pressure for 7 hours. Then, each of these was admixed with dry chips of polyethylene terephthalate (an intrinsic viscosity=0.640 in phenol tetrachloroethane (6:4)) in an amount to provide a concentration of 10% by weight of the copper-zeolite. Each mixture obtained was melted at 270° C. and extruded to form coarse strands which were then cooled and cut to yield three types of master chips. Each type of master chips and polyethylene terephthalate chips having no zeolite were dried to a water content of 0.01% and fed at a ratio of 1 to 2 to conduct conjugate spinning and drawing which gave three types of conjugated yarns having a fineness of 50 deniers / 5 filaments and a cross-sectional form shown in FIG. 1. In FIG. 1, A is a polyester component containing zeolite and B is a polyester component containing no zeolite.

Then each yarn thus obtained was doubled with a usual drawn yarn of polyethylene terephthalate having a fineness of 50 deniers/36 filaments and circular-knitted. Each knitted fabric was scoured and subjected to the test for evaluation of an antibacterial effect on *Escherichia coli*. In every case, the formation of an inhibition zone was observed. thus, the bactericidal effect was confirmed.

Comparison Example 2

Each of fine, dry powder of unconverted $Z_1$, $Z_3$ and $Z_4$ as described in Table 1 was admixed with polyethylene terephthalate and spun to obtain conjugated yarns having a fineness of 50 deniers/5 filaments, according to the same procedure as in Example 2. The test for evaluation of an antibacterial effect was conducted on a circular knitted fabric made of the above yarns. In every case, the formation of an inhibition zone was not observed. Thus, no effect was confirmed.

Comparison Example 3

To 250 g of the fine dry powder of the A-type zeolite ($Z_1$) as described in Table 1 was added 1000 ml of an aqueous 1M copper sulfate solution and the resultant mixture was stirred for 5 hours at room temperature. The copper-A-type zeolite thus obtained was filtered by suction, washed with water until the sulfate ion disappeared, dried at 100°–105° C., and then pulverized to provide fine powder of the copper-A type zeolite. The converted copper-A-type zeolite thus obtained contained $Cu_3(SO_4)(OH)_4$ as deposition thereof.

The converted copper-A-type zeolite was admixed with polyester and spun to obtain conjugated yarns having a fineness of 50 deniers/5 filaments, as described in Example 2. The test of evaluation of an antibacterial effect was conducted as described in Example 2 and no formation of an inhibition zone was observed. Thus, no effect was confirmed.

EXAMPLE 3

The zinc-A-type zeolite ($Z_{17}$) and the zinc-X-type of zeolite ($Z_{18}$) as described in Table 2 were dried at 200° C. at a reduced pressure for 7 hours. Then, each of the dried powder was admixed with a solution containing 25% by weight of an acrylic copolymer (components: acrylonitrile, 10 wt. % of methyl acrylate and 1 wt. % of sodium acrylsulfonate) in DMF in an amount to provide 5% by weight, based on the polymer, of the metal-zeolite. The mixture thus obtained was wet spun, drawn and cut according to a conventional technique to give two types of acrylic staple having a fineness of 3 deniers and a length of 51 mm. The staple was then spun into single yarns having a No. 30 yarn count according to a conventional manner, and circular-knitted and scoured, followed by the measurement of an extinction rate of Eumycetes as a test of a bactericidal effect. The results are shown in Table 6.

TABLE 6

| | Extinction rate of Eumycetes | |
|---|---|---|
| | Zeolite added in an acrylic copolymer | |
| Eumycetes | $Z_{17}$ | $Z_{18}$ |
| Aspergillus flavus | 80% | 55% |

As can be seen from Table 6 the acrylic fiber containing the zinc-zeolite according to the present invention has a considerable bactericidal effect.

Comparison Example 4

Each of the dry fine powder of the unconverted zeolites $Z_1$ and $Z_2$ was admixed with the acrylic copolymer, spun and cut into staple (3 deniers, 51 mm length) and then spun into single yarns having a No. 30 yarn count. The extinction test was conducted on a circular knitted fabric made of the above yarns in the same manner as described in Example 3 to give the result of 0% of the extinction rate. Thus, no effect was observed.

EXAMPLE 4

Each of the silver-A-type zeolite ($Z_7$), the silver-natural mordenite ($Z_{11}$), the silver-natural chabazite ($Z_{12}$), the copper-natural chabazite ($Z_{16}$) and the zinc-natural mordenite ($Z_{19}$) was dried at 200° C. at a reduced pressure for 7 hours.

Then, the dried powder was admixed with dry powder of polybutylene terephthalate (an intrinsic viscosity $\eta = 1.10$ in phenol tetrachloroethane (6:4)) in various amounts and injection moulded at 240° C. into a disc having a diameter of 20 mm and a thickness of 3 mm. The use of the materials containing more than 50% by weight of the metal-zeolite resulted in moulded discs having an uneven surface on account of the poor fluidity of the melted materials. The addition of not more than 50% did not cause the above problem and, especially, the addition of not more than 40% yielded the articles invariably having good physical properties. Bactericidal effects of the resulting discs were evaluated by the extinction rates of Eumycetes which are summarized in Table 7.

TABLE 7

| Zeolite and metal content therein | | | Extinction rate Amount of zeolite added (wt. %) | | | |
|---|---|---|---|---|---|---|
| | | | 30 | 3 | 0.3 | 0.03 |
| $Z_7$ | Ag | 2.39 | 100 | 100 | 92 | 45 |
| $Z_{11}$ | Ag | 0.25 | 100 | 88 | 71 | 5* |
| $Z_{12}$ | Ag | 0.19 | 100 | 87 | 74 | 4* |
| $Z_{16}$ | Cu | 0.11 | 90 | 58 | 7* | 0* |
| $Z_{19}$ | Zn | 0.85 | 80 | 62 | 50 | 3* |

*These are evaluated as having no antibacterial effect.

It is understandable from the table that metal ion concentration above a certain level is required to obtain a satisfactory result depending on both a metal content in zeolite and an amount of added zeolite. The polymer articles which meet the aforementioned requirement according to the present invention have an excellent antibacterial effect.

EXAMPLE 5

Figure 2:
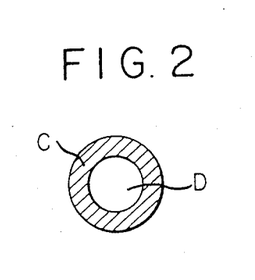

Each of the unconverted A-type zeolite ($Z_1$), the X-type zeolite ($Z_2$), the Y-type zeolite ($Z_3$) and the natural mordenite ($Z_4$) as described in Table 1 was dried at 200° C. at a reduced pressure for 7 hours and, then, admixed with dry chips of Nylon 6 ($\eta$ rel = 2.3) in an amount to provide 0.5% by weight of zeolite. The mixture was fed to one side of a conjugate spinning machine and Nylon 6 chips with no zeolite was fed to the other side of the spinning machine at a ratio of feeds of 1 to 1. After spinning and drawing, four types of conjugated yarns having a cross-sectional shape shown in FIG. 2 and a fineness of 100 deniers/24 filaments were obtained. In FIG. 2, C is a Nylon 6 component containing zeolite and D is a Nylon 6 component with no zeolite. The yarns were circular-knitted and scoured. 10 g of each knitted fabric thus made was soaked in 100 ml of an aqueous 1/500M silver nitrate solution and was stirred at room temperature for 20 hours to perform an ion exchange reaction. Thereafter, the knitted fabric was sufficiently washed with water, dried and subjected to measurement of a silver content and evaluation of an anti-bacterial effect. The results are summarized in Table 8.

TABLE 8

| | Zeolite added to Nylon 6 | | | |
|---|---|---|---|---|
| | $Z_1$ | $Z_2$ | $Z_3$ | $Z_4$ |
| | Silver content, based on total amount of zeolite added | | | |
| Evaluation of antibacterial effect | 3.20 | 2.92 | 2.48 | 1.80 |
| Escherichia coli | + | + | + | − |
| Pseudomonus aeruginosa | + | + | + | + |
| Staphylococcus aureus | + | + | + | + |

TABLE 8-continued

| | Zeolite added to Nylon 6 | | | |
|---|---|---|---|---|
| | $Z_1$ | $Z_2$ | $Z_3$ | $Z_4$ |
| | Silver content, based on total amount of zeolite added | | | |
| Evaluation of antibacterial effect | 3.20 | 2.92 | 2.48 | 1.80 |
| *Candida alvicans* | + | + | + | + |

It is apparent from Table 8 that the polymer article according to the present invention could be produced by the second alternative process to show an excellent bactericidal effect.

EXAMPLE 6

This Example shows the adverse effect of a saturating amount of a bacteriocidal metal ion on the bacteriocidal properties of the zeolite-metal ion.

The Comparison Example was conducted according to French Pat. No. 1,061,158, Example 1.

Commercially available zeolite fine powder (mordenite, $SiO_2/Al_2O_3$ mol ratio: about 10) was used. The mordenite was pretreated by a 2M NaCl aqueous solution for regeneration to ensure that the ion-exchangeable metal in the mordenite would be sodium, then washed with water to remove excess NaCl.

Sample 6-1

To 1 kg of the mordenite were added about 2 liters of a 0.7M $Cu(NO_3)_2$ aqueous solution with stirring, to which diluted $NHO_3$ was then added, little by little with continuous stirring, to finally regulate the pH of the mixture to 3.1. The mixture was stirred at room temperature for an additional 5 hours to proceed with conversion to copper-mordenite. The converted zeolite was separated and washed with water to remove excessive copper ions from the solid phase, and then dried. About 890 g of the dried converted zeolite were obtained, which contained 2.6%, dry basis, of copper. 2.6% of copper corresponds to 41% of the calculated ion exchange capacity of this mordenite.

Sample 6-2

To 1 kg of the mordenite were added about 2 liters of an aqueous solution of 0.9M $CuSO_4$ with stirring, to which diluted $H_2SO_4$ was then added little by little with continuous stirring to finally regulate a pH of the mixture to 2.9. The mixture was stirred at room temperature for an additional 3 hours to proceed with conversion to copper-mordenite. The solid mordenite was separated, to which were further added 1.5 liters of a 0.9M $CuSO_4$ aqueous solution and the above procedure was repeated. The converted zeolite after the second treatment was separated, washed with water to remove excessive copper ion from the solid phase, and dried. About 930 g of the dried converted zeolite were obtained, which contained 4.5%, dry basis, of copper. 4.5% of copper corresponds to 71% of the calculated ion exchange capacity of this mordenite.

Comparison Example

To 100 g of the mordenite were added about 250 ml of a 2M $CuSO_4$ aqueous solution and stirred for 4 hours. Then the solid mordenite was separated, to which were further added about 250 ml of a 2M $CuSO_4$ aqueous solution and the above procedure was repeated. The resultant converted zeolite, after washing was dried, which contained 6.3%, dry basis, of copper. 6.3% of copper means almost complete saturation of the ion exchange capacity of this mordenite.

The three converted zeolites were tested for bacteriocidal effects by the bacteriocidal activity test with the disc method, as explained above, with the exception that instead of a disc the zeolite particles were dusted over the medium. The results are summarized in Table 9.

TABLE 9

| | Sample | | | |
|---|---|---|---|---|
| Bacteria or Eumycetes | Sample 6-1 | Sample 6-2 | Comparison Example | Unconverted mordenite |
| *Escherichia coli* | + | + | not tested | — |
| *Staphylococcus aureus* | + | + | — | — |
| *Pseudomonus aeruginosa* | not tested | + | — | — |

+ = Presence of an inhibition zone
− = Absence of an inhibition zone

We claim:

1. A polymer article having antibacterial properties in which the polymer article comprise at least one polymer and 0.01 to 10% by weight, based on the total weight of the polymer article, of zeolite particles having a specific surface area of at least 150 m²/g, based upon anhydrous zeolite as the standard, and an $SiO_2/Al_2O_3$ mol ratio of at most 14, provided that the zeolite particles retain at least one metal ion having bacteriocidal properties at ion-exchangeable sites of the zeolite in an amount less than 92 percent of the ion exchange capacity of the zeolite.

2. The polymer article as claimed in claim 1, in which the zeolite particles are composed of A-type zeolite, X-type zeolite, Y-type zeolite, mordenite or a mixture thereof.

3. The polymer article as claimed in claim 1, in which the metal ion is selected from silver, copper and zinc ions.

4. The polymer article as claimed in claim 1, in which the zeolite content is in a range of from 0.05 to 10% by weight, based on anhydrous zeolite.

5. The polymer article as claimed in claim 1, in which the polymer article is in the form of a fiber, a film or a granule.

6. The polymer article as claimed in claim 1, in which the zeolite particles retain the metal ion in an amount of less than 85 percent of the ion exchange capacity of the zeolite.

7. The polymer article as claimed in claim 6, in which the zeolite particles retain the metal ion in an amount of less than 70 percent of the ion exchange capacity of the zeolite.

8. A shaped article in the form of a fiber, a film or a granule having antibacterial properties consisting essentially, in percent by weight of the entire shaped article, of:
   90 to 99.9% of a polymeric substrate having dispersed therein;
   from 0.1 to 10% of zeolite particles having a specific surface are of at least 150 m²/g, based upon anhydrous zeolite as the standard, and an $SiO_2/Al_2O_3$ mol ratio of at most 14, wherein the zeolite particles retain at least one metal ion having bacteriocidal properties at ion-exchangeable sites of the zeolite in an amount less than 92 percent of the ion exchange capacity of the zeolite.

9. A process for producing a polymer article having antibacterial properties in which the polymer article comprises at least one polymer and 0.1 to 10% by weight, based on the total weight of the polymer article, of zeolite particles having a specific surface area of at least 150 m²/g, based upon anhydrous zeolite as the standard, and an $SiO_2/Al_2O_3$ mol ratio of at most 14, wherein the zeolite particles retain at least one metal ion having bacteriocidal properties at ion-exchangeable sites of the zeolite in an amount less than 92 percent of the ion exchange capacity of the zeolite, said process comprising the steps of:
(a) admixing the zeolite particles, which retain at least one metal ion having bacteriocidal properties at ion-exchangeable sites of the zeolite in an amount less than 92 percent of the ion exchange capacity of the zeolite, with the polymer or a mixture of such polymers, and thereafter
(b) moulding the polymer/zeolite admixture to form a shaped article.

10. A process for producing a polymer article having antibacterial properties in which the polymer article comprises at least one polymer and 0.01 to 10% by weight, based on the total weight of the polymer article, of zeolite particles having a specific surface area of at least 150 m²/g, based upon anhydrous zeolite as the standard, and an $SiO_2/Al_2O_3$ mol ratio of at most 14, said process comprising the steps of:
(a) molding a polymer or a mixture of polymers containing said zeolite particles dispersed therein, and then
(b) treating the thus-molded article with an aqueous solution of at least one water-soluble salt of at least one metal ion having bacteriocidal properties to provide the zeolite particles with said metal ion at ion-exchangeable sites of the zeolite in an amount less than 92 percent of the ion exchange capacity of the zeolite.

11. The process as claimed in claim 10, in which the aqueous solution contains silver ions.

12. The process as claimed in claim 10, in which the aqueous solution contains copper ions.

13. The process as claimed in claim 10, in which the aqueous solution contains zinc ions.

14. The process as claimed in claim 9, in which the article is moulded in step (b) into a fiber, a film or a granule.

15. The process as claimed in claim 10, in which the article moulded in step (a) is in the form of a fiber, a film or a granule.

* * * * *